United States Patent [19]
Schueler

[11] Patent Number: 6,114,326
[45] Date of Patent: Sep. 5, 2000

[54] USE OF CABERGOLINE IN THE TREATMENT OF RESTLESS LEGS SYNDROME

[75] Inventor: Peter Schueler, Erlangen, Germany

[73] Assignee: Pharmacia & Upjohn Company, Kalamazoo, Mich.

[21] Appl. No.: 09/275,739

[22] Filed: Mar. 24, 1999

Related U.S. Application Data

[63] Continuation of application No. PCT/US99/04269, Mar. 24, 1999.
[60] Provisional application No. 60/079,639, Mar. 27, 1998.
[51] Int. Cl.$^7$ .................................................. A61K 31/48
[52] U.S. Cl. .......................... 514/220; 514/221; 514/284; 514/285; 514/288; 514/289; 514/323; 514/923
[58] Field of Search .................................. 514/220, 221, 514/284, 285, 288, 289, 323, 923

[56] References Cited

U.S. PATENT DOCUMENTS

| | | | |
|---|---|---|---|
| 4,526,892 | 7/1985 | Salvati et al. ............................ | 518/288 |
| 5,496,836 | 3/1996 | Di Rocco et al. ....................... | 514/370 |

OTHER PUBLICATIONS

JE Ahlskog, et al., "Adjunctive Cabergoline Therapy of Parkinson's Disease: Comparison with Placebo and Assessment of Dose Response and Duration of Effect," Clin. Neuropharmacol, 1996; 19:202–212.
S Akpinar, "Restless Legs Syndrome Treatment with Dopaminergic Drugs," Clinical Neuropharmacology, 1987; 10:69–79.
RP Allen, "Augmentation of the Restless Legs Syndrome with Carbidopa/Levodopa," Sleep, 1996; 19(3):205–13.
Anonymous, " Carbergolin: Neue Horizonte in der Therapie des Morbus Parkinson," Nervenarzt (1998 Sep.) 69 (Suppl Neue Horiz) 1–8, XP002116346.
Anonymous, "Cabergoline: New Horizons in Parkinson's Disease Treatment,"—Translated version of XP0021116346, pp. 1–17 (1998).
Atlas Task Force of the American Sleep Disorders Association, Recording and Scoring Leg Movements, Sleep, 1993; 16:748–759.
PM Becker, AO Jamieson, WD Brown, "Dopaminergic Agents in Restless Legs Syndrome and Periodic Limb Movements in Sleep: Response and Complications of Extended Treatment in 49 Cases," Sleep, 1993; 16:713–716.
D Boghen, et al., "The Treatment of Restless legs Syndrome with Clonazepam: A Prospective Controlled Study," Can J Neurol Sci, 1986; 13:245–247.
DB Boivin, D Lorrain, J Montplaisir, "Effects of Bromocriptine on Periodic Limb Movements in Human Narcolepsy," Neurology 1993; 43:2134–2136.
B Bornstein, "Restless Legs," Psychiat Neurol, 1961; 141:165–201.1.
C Brodeur, J Montplaisir, R Marinier, "Treatment of RLS and PMS with L–dopa: A Double–Blind Controlled Study," Neurology; 35:1845–1848. (1988).

V Collado–Seidel, et al., A Controlled Study of Additional sr–L–dopa in L–dopa–Responsive Restless Legs Syndrome with Late–Night Symptoms,Neurology, 1999, 52:285–290.
N Callaghan, "Restless Legs Syndrome in Uremic Neuropathy," Neurology, 1966, 16:359–361.
RM Coleman, "Periodic Movements in Sleep (Nocturnal Myoclonus) and Restless Legs Syndrome." In: Guilleminault C, (ed) Sleeping and Walking Disorders: Indications and Techniques, 1982, Menlo Park: Addison Wesley; 265–295.
CJ Earley, RP Allen, "Pergolide and Carbidopa/Levodopa Treatment of the Restless Legs Syndrome and Periodic Leg Movements in Sleep in a Consecutive Series of Patients," Sleep, 1996; 19(10):801–10.
KA Ekbom, "Restless Legs," Acta Medica Scandinavica, 1945 ; suppl. 158: 1–123.
KA Ekbom, "Restless Legs Syndrome," Neurology, 1960; 10:868–873.
RG Fariello, "Pharmacodynamic and Pharmacokinetic Features of Carbergoline," Drugs, 1997, 55:S2, 10–16.
A Feigen, "Restless Legs Syndrome," JAMA, 1995; 274 (15) 1191–2.
B Frankel, "Restless Legs Syndrome," JAMA, 1974; 230:1302–1303.
C Gorman, et al., "Symptoms of Restless Legs," Arch Intern Med, 1965; 115:155–60.
C Guilleminault, M Cetel, P Philip, "Dopaminergic Treatment of Restless Legs and Rebound Phenomenon," Neurology, 1993; 43(2):445.
D Harriman, et al., "Ekbom's Syndrome and Burning Paraesthesiae," Brain, 1970; 93:393–406.
EM Heiman, et al., "Lithium–Aggravated Nocturnal Myoclonus and Restless Legs Syndrome [letter]," American Journal of Psychiatry, 1986; 143:1191–1192.
F Heinze, et al., "Restless Legs and Orthostatic Hypotension in Primary Amyloidosis," Arch Neurol, 1967; 16:497–500.
W Hening, et al., "The Cortical Premovement Potentials of RLS Jerks," Sleep Res, 1991; 20:255.
WA Hening, et. al., "Dyskinesias While Awake and Periodic Movements in Sleep in Restless Legs Syndrome: Treatment with Opioids," Neurology; 1986; 36:1363–1366.
S Iannaccone, et al., "Evidence of Peripheral Axonal Neuropathy in Primary Restless Legs Syndrome," Movement Disorders, 1995; 10:2–9.
PW Kaplan, RP Allen, DW Suchholz, JK Walters, "A Double–Blind, Placebo Controlled Study of the Treatment of Periodic Limb Movements in Sleep Using Carbidopa/ Levodopa and Propoxyphene," Sleep, 1993; 16:717–723.
S Kotagal, et al., "Nocturnal Myoclonus—A Sleep Disturbance in Children with Leukemia," Annals of Neurology, 1984; 16:392.

(List continued on next page.)

Primary Examiner—Frederick Krass
Attorney, Agent, or Firm—Thomas A. Wootton

[57] ABSTRACT

The present invention provides for the use of cabergoline and other agents for the treatment of restless legs syndrome (RLS).

24 Claims, No Drawings

OTHER PUBLICATIONS

C Kramer, M Kerkjarto, B Leplow, EO Krasemann, "LebensqualitätsmeSsungen im wöchentlich erhobenen Verlauf bei Herzinfarktpatienten," Psychother Psychosom Med Psychol, 1990; 40:409–416.

E Lugaresi, et al., "Nocturnal Myoclonus and Restless Legs Syndrome," In: S Fahn et al. (eds), Advances in Neurology, 1986, vol. 43: Myoclonus, New York: Raven Press; 295–307.

P Martinelli, et al., "Nocturnal Myoclonus, Restless Legs Syndrome, and Abnormal Electrophysiological Findings," Ann Neurol, 1987; 21:515.

WB Matthews, "Iron Deficiency and Restless Legs," Br Med J, 1976; 1–898.

M Miyagi, et al., "Dopamine Receptor Affinities in vitro and Stereotypic Activities in Vivo of Cabergoline in Rats," Biol. Pharm. Bull., 1996; 19L 1210–1213.

H Moldofsky, et al., "Sleep–Related Myoclonus in Rheumatic Pain Modulation Disorder (Fibrositis Syndrome) and in Excessive Daytime Somnolence," Psychosomatic Medicine, 1984; 46:145–151.

J Montplaisir, et al., "Familial Restless Legs with Periodic Movements in Sleep:Electrophysiologic, Biochemical, and Pharmacological Study," Neurology, 1985; 35:130–134.

J Montplaisir, et. al., "Restless Legs Syndrome and Periodic Movements in Sleep: Physiopathology and Treatment with L–dopa," Clinical Neuropharmacology, 1986; 9:456–463.

SS Mosko, et al., "Somatosensory and Brainstem Auditory Evoked Responses in Sleep–related Periodic Leg Movements," Sleep, 1986; 9:399–404.

W Ondo, "Ropinirole for Restless Legs Syndrome," Movement Disorder; 14:138–140 (1999).

G Reynolds, et al., "Restless Leg Syndrome and Rheumatoid Arthritis," British medical Journal, 1986; 292:659–660.

UK Rinne, et al: "Cabergoline in the Treatment of Early Parkinson's Disease: Results of the First Year of Treatment in a Double–Blind Comparison of Cabergoline and Levodopa," Neurology, 1997, 48/2 (363–368). XP002116347.

E Ruiz–Primo, Is Nocturnal Myoclonus a Common Sleep Disturbance in Children with Leukaemia, Dev Med Child Neurol, 1987; 29:833.

F Salvi, et al., "Restless Legs Syndrome and Nocturnal Myoclonus: Initial Clinical Manifestation of Familial Amyloid Polyneuropathy," J Neurol Neurosurg Psychiatry, 1990; 53:522–525.

R Sandyk, et al., "L–Dopa in Uremic Patients with the Restless Legs Syndrome," Int J Neurosci, 1987; 35:233–235.

MH Silber, JW Shepard, Jr., JA Wisbey, "Pergolide in the Management of Restless Legs Syndrome: An Extended Study," Sleep, 1997; 20(10): 878–82.

JD Spillane, "Restless Legs Syndrome in Chronic Pulmonary Diseases," Br Med J, 1970; 4:796–798.

K Stiasny, et al., "Treatment of Restless Leg Syndrome (RLS)with Cabergoline" ENS, Nice Abstract, 1988.

MJ Thorpy, Chairman, Diagnostic Classification Steering Committee in International Classification of Sleep Disorders: Diagnostic and Coding Manual, 1990, American Sleep Disorders Association.

C Trenkwalder, et al., "L–Dopa in Uremic and Idiopathic Restless Legs Syndrome:A Double–Blind, Crossover Trial," Sleep, 1995; 18:681–688.

PT Trzepacz, et. al., "Response to Opioids in Three Patients with Restless Legs Syndrome," Ann J Psychiatry, 1984; 141:993–995.

C Von Scheele, "Levodopa in Restless Legs," Lancet, 1986; 2:426–427.

C Von Scheele, V Kempi, Long–Term Effect of Dopaminergic Drugs in Restless Legs. A 2–Year Follow–up, Arch Neurol, 1990; 47:1223–1224.

SL Walker, A Fine, MH Kryger, "L–Dopa/Carbidopa for Nocturnal Movement in Uremia," Sleep, 1996; 19:213–218.

AS Walters, et al., "A Double–Blind Randomized Crossover Trial of Bromocriptine and Placebo in Restless Leg Syndrome," Ann Neurol, 1988; 24:455–458.

AS Walters, "Toward a Better Definition of the Restless Legs Syndrome," The International Restless Legs Syndrome Study Group., Mov Disord, 1995; 10(5):634–42.

JC Ware, et al., "Nocturnal Myoclonus and Tricyclic Antidepressants," Sleep Research, 1984; 13:72.

S Watanabe, et al., "Periodic Legs Movements During Either Epidural or Spinal Anesthesia in an Elderly Man without Sleep–related (Nocturnal) Myoclonus," Sleep, 1990; 13:262–266.

LR Wechsler, et al., "Periodic Leg Movements of Sleep (Nocturnal Myoclonus): An Electrophysiological Study," Annals of Neurology ,1986; 19:168–173.

TC Wetter, K Stiasny, J Winkelmann, A Buhlinger, U Brandenburg, T Penzel, et al. A Polysomnographic, Controlled Study of Pergolide in the Treatment of Restless Legs Syndrome, *Neurology,* 1998; 50(4):A69.

J Winkelman, TC Wetter, K Stiasny, WH Oertel, C Trenkwalder, Treatment of Restless Leg Syndrome with Pergolide—An Open Clinical Trial, *Mov. Disord 1998;* 13 (3):566–9.

USE OF CABERGOLINE IN THE TREATMENT OF RESTLESS LEGS SYNDROME

CROSS-REFERENCE TO RELATED APPLICATIONS

This application claims the benefit of U.S. provisional application Ser. No. 60/079,639 filed Mar. 27, 1998, under 35 USC §119(e)(i) and is a continuation of PCT/US99/04269, filed Mar. 24, 1999.

FIELD OF THE INVENTION

The present invention relates to the use of cabergoline, and the pharmacologically acceptable salts thereof, in the treatment of restless leg syndrome.

BACKGROUND OF THE INVENTION

Restless leg syndrome (RLS) is a neurosensorimotor disorder with parestethasias, sleep disturbances and, in most cases, periodic limb movements of sleep (PLMS).

Two forms of RLS appear to exist: The idiopathic and the uremic form. In this document both forms will be referred to as RLS. RLS, or restless legs syndrome, is characterized by (1) a desire to move the legs, usually associated with paresthesias/dysesthesias, (2) motor restlessness, (3) worsening or exclusive presence of symptoms at rest (i.e. lying, sitting) with at least partial or temporary relief by activity, and (4) worsening of symptoms during the evening or night. According to the International RLS Study Group, these four minimal criteria already allow clinical diagnosis. RLS is considered by some to be a sleep disorder in which a person experiences unpleasant sensation in the legs described as creeping, tingling, pulling, or painful. One or both legs may be affected. The sensations occur when the person with RLS lies down or sits for prolonged periods of time, such as at a desk, riding in a car, or watching a movie. RLS symptoms worsen during periods of relaxation and decreased activity. The evening and night hours tend to be more troublesome for RLS suffers.

Sensory and motor symptoms in RLS often result in severe sleep disturbances with prolonged sleep latency, decreased total sleep time with reduced or absent slow wave sleep and decreased sleep efficiency. RLS patients often sleep best toward the end of the night or during the morning hours. Because of less sleep at night, people with RLS may feel sleepy during the day on an occasional or regular basis. Almost all RLS patients present periodic leg movements (PLM) during sleep (PLMS) and also while being awake. The number of PLM and related parameters are considered to be a marker for the severity of RLS since PLM are frequently associated with nocturnal arousals or awakenings and if present during wakefulness may prevent patients from falling asleep. Therefore performing polysomnography is usually needed to evaluate the efficacy of drug therapies.

As a result of problems both in sleeping and while awake, people with RLS may have difficulties with their job, social life, and recreational activites. RLS is reasonably common and always distressing. In the past some have called it "Crazy Legs." RLS sensations have been described as pulling, drawing, crawling, wormy, boring, tingling, pins and needles, prickly and sometimes painful sensations that are usually accompanied by an overwhelming urge to move the legs. Sudden muscle jerks may occur.

Various agents have been used to treat RLS. However no substance is currently approved for this indication.

Over the years, several treatments have been proposed for RLS. Typically treatments are grouped into four catagories: anticonvulsant drugs, benzodiazepines, opioids and dopaminergic agents.

Anticonvulsants. Several anticonvulsant drugs have been tested for use in treating RLS. Anticonvulsants appear to work by decreasing sensory disturbances (the unpleasant sensations) and the urge to move. These drugs are particularly effective for some, but not all, patients with marked daytime symptoms, particularly people who have pain syndromes associated with their RLS. Gabapentin (Neurontin) is the anticonvulsant that has shown the promise in treating the symptoms of RLS. Possible side effects of gabapentin include dizziness, sleepiness, fatigue, increased appetite, and unsteadiness. The sedative properties of gabapentin may impair the ability to operate heavy machinery, including a motor vehicle.

Benzodiazepines. Several benzodiazepines, including clonazepam (Klonopin), nitrazepam, lorazepam and temazepam, have been used to treat RLS and sometimes improve the quality of nocturnal sleep. Benzodiazepines are central nervous system depressants that do not fully suppress RLS sensations or leg movements, but allow patients to obtain more sleep despite the problems. Some drugs in this group result in daytime drowsiness.

Opioids are narcotic analgesic (pain-killing) drugs and relaxing drugs that can suppress RLS and PLMS in some people especially those with severe and relentless symptoms of RLS. Some examples of medications in this category include codeine, propoxyphene (Darvon or Darvocet), oxycodone (Percocet, Tylox, Roxiprin), pentazocine (Talwin), hydrocodone (Vicodin), and methadone.

The therapeutic action of opioids was mentioned in the original description of RLS by Ekbom. Recently, this effect has been further documented in open clinical trials, see, Trzepacz P T, Violette E J, Sateia M J (1984). Response to opioids in three patients with restless legs syndrome. *Am J Psychiatry;* 141:993–995. and Hening W A, Walters A, Kavey N, Gidro-Frank S, Cote L, Fahn S (1986). Dyskinesias while awake and periodic movements in sleep in restless legs syndrome: treatment with opioids. *Neurology;* 36:1363–1366. (1986). In these studies RLS was found to be reversible by naloxone, an opioid receptor antagonist. Opioids are potent suppressors of RLS and PLMS, but they carry the risk for abuse and the danger of addiction limit. Side effects and adverse reactions include dizziness, sedation, nausea, vomiting, constipation, hallucination, and headache. In severe cases, however, and especially in those undergoing hemodialysis, opiates may be an alternative treatment.

Dopaminergic drugs have produced some interesting results. Dopaminergic agents are drugs that are usually used to treat Parkinson's disease and in some cases may appear to provide some short term relief for some people with RLS. RLS is not a form of Parkinson's disease but is a distinct neurologic condition. Several studies have shown that L-dopa given with a peripheral carboxylase inhibitor at a 10:1 ratio is effective in treating RLS. See for example the following articles: Brodeur C, Montplaisir J, Marinier R, Godbout R., "Treatment of RLS and PMS with L-dopa: a double-blind controlled study," *Neurology;* 35:1845–1848 (1988). Montplaisir J, Godbout R, Poirier G, Bedard M. A., "Restless legs syndrome and periodic movements in sleep: physiopathology and treatment with L-dopa," *Clinical Neuropharmacology;* 9:456–463 (1986). Von Scheele C, "Levodopa in restless legs," *Lancet;* 2:426–427 (1986). Akpinar S., "Restless legs syndrome treatment with dopaminergic drugs," *Clinical Neuropharmacology;* 10:69–79 (1987).

A controlled study using polysomnography (PSG) recordings in a double-blind design also showed that L-dopa administered twice at night produces a significant reduction of RLS occurring at bedtime and of PLMS throughout the night. Brodeur C, Montplaisir J, Marinier R, Godbout R., "Treatment of RLS and PMS with L-dopa:

a double-blind controlled study," *Neurology;* 35:1845–1848 (1988). In most cases, L-dopa 100 mg, in conjunction with the decarboxylase inhibitor carbidopa 10 mg, completely suppresses RLS although a rebound (augmentation) of PLMS is often observed in the last part of the night. Montplaisir J, Godbout R, Poirier G, Bédard M. A., *Clinical Neuropharmacology;* 9:456–463 (1986). The two major side effects frequently seen in patients treated with L-dopa are: 1) a rebound of symptoms during daytime when patients are only treated at night; and 2) a single dose of L-dopa at bedtime decreases PLMS in the first third of the night but induces a rebound of these movements in the last third of the night when L-dopa is no longer effective. Id. Similarly, the same study showed that when L-dopa treatment is repeated in the middle of the night, patients with severe cases may experience de novo paraesthesia and restlessness during the daytime.

Bromocriptine, a D2 receptor agonist, was also used in RLS treatment. Walters A S, Hening W A, Chokroverty S, Gidro-Franck S. A double blind randomized crossover trial of bromocriptine and placebo in restless leg syndrome. *Ann Neurol;* 1988, 24:455–458. (1988). After a dose of 7.5 mg was administered 1 to 3 hours prior to sleep, 5 of 6 patients reported better subjective improvement in restlessness and paresthesia compared to placebo. Side effects reported were transient nasal stuffiness and lightheadedness in one patient.

Pergolide, the dopamine D1/D2 agonist, (half-life 7–16 hours) in combination with a low dose of L-dopa can lead to clinical improvement in patients who do not respond to L-dopa alone, but can also cause several important side effects such as orthostatic hypotension and gastrointestinal problems.

The Internet RLS site, http://www.rls.org, had the following to say about dopaminergic drug treatments. Note, the Internet site my be updated at any time, the following quotes were copied in March 1999. "The primary and first-line treatment for RLS is with dopaminergic agents, which work in the central nervous system by enhancing the levels of dopamine, a chemical that the body naturally produces and that regulates the delivery of messages between cells in the nervous system." But then the site provides this warning: "The dopaminergic agent that has been used most often is carbidopa-levodopa (Sinemet® DuPont-Merck). The advantages to using Sinemet® are that this drug has been available the longest and it is the least-expensive dopaminergic agent. However, Sinemet® does have one very important disadvantage: up to 85% of people who take this drug for the treatment of RLS develop a phenomenon known as augmentation." The site provides another description of augmentation. "What happens with augmentation is this: the usual dose of Sinemet® will allow you to obtain relief from your symptoms so that you will be able to sleep at night, but the sensations, the need to move, and the restlessness will develop (frequently with an increased intensity) earlier in the day (during the afternoon or even during the morning). If this happens, you may be tempted to increase your dose of Sinemet to treat these daytime symptoms, but that would be the wrong approach. If augmentation does develop, increasing your dosage of Sinemet® will only worsen rather than improve your symptoms. Most people with RLS who develop augmentation must switch to another medication."

"Though Sinemet® does work well for many people and has minimal side effects (primarily gastrointestinal discomfort, nausea, vomiting, and headache), every person who takes this drug for the treatment of RLS needs to clearly understand the potential for developing augmentation. One other consideration that you should understand is that because protein interferes with the absorption of Sinemet®, you should avoid consuming a high-protein meal just before taking this medication."

The Internet site continues and discusses other possible treatments.

"A newer drug, pergolide mesylate (Permax®), is showing great promise in treating RLS. Recent studies have shown that this medication is as effective as Sinemet® and has much less potential for causing augmentation (10% for Permax® vs. 80% for Sinemet®). The disadvantages of Permax® are that it is more expensive than Sinemet® and it has not been used as long, so that physicians are less familiar with prescribing this drug. The primary side effects are dizziness, nausea, and nasal congestion."

"Bromocriptine mesylate (Parlodel®) is another dopaminergic agent that is used to treat RLS. Results of studies regarding the effectiveness of bromocriptine are mixed, although individual patients have reported good results."

"Permax® and Parlodel® are both dopamine-receptor agonists, meaning that they work at the dopamine-binding site, while Sinemet® augments the body's normal production of dopamine. Other studies suggest that patients treated with Permax® (pergolide) will develop tolerance to the drug."

Considering the problems with all the possible treatments mentioned above, it is fair to say, there is no optimally effective treatment for RLS. An RLS patient who turns to the Internet and sees the above comments will be overwhelmed with possible treatments, such as, iron supplements, melatonin, Prozac®, Sinement®, Klonopin®, clonazepam, all the drug and drug catagories mentioned above and even electrical stimulation to the legs or feet before bedtime. See http://www.rls.org. On the Internet one can find the suggestion that there is no good treatment regime for RLS, that medical books will list over 15 different treatments or protocols but that none of them are very effective. The following quote from an RLS suffer is posted on the Internet RLS site. "I feel as if worms are creeping and crawling in my legs. I need to wiggle my legs to make the feelings go away. Sometimes, in the evening, when I'm driving or just sitting at the movies or watching TV, I want to keep moving my legs. I want to just hit them with a hammer." http://www.rls.org Currently a physician might be tempted to use levodopa in conjunction with a dopa decarboxylase inhibitor (DDCI) such as carbidopa. Controlled studies with levodopa have proven the beneficial effects on subjective RLS symptoms and sleep quality confirmed by polysomnographic studies. Since regular release formulas often do not maintain therapeutic coverage throughout the night, sustained release formulas are attempted. Although many RLS patients show an excellent response to levodopa there is increasing evidence that the relatively short duration of action and augmentation of symptoms may be a limiting factor of levodopa therapy.

Augmentation is described above, it comprises an earlier onset of RLS symptoms in the evening than before treatment, appearance of symptoms during the day, an involvement of other body parts (i.e. the arms) or an increased severity of symptoms. Therefore, alternative treatment options are of major interest especially in patients with severe RLS. The choice of where to turn for a possible treatment of RLS is a problem for any treating physician, with the possible known treatments presenting serious drawbacks. Here we present a novel approach to treating RLS and we present a preferred approach to this problem that appears to be the first good treatment for this serious common distressing medical syndrome.

INFORMATION DISCLOSURE STATEMENT

The following references refer to RLS and its possible treatments. To the extent this information may be useful to one skilled in the art or to more fully describe this invention, it is incorporated herein by reference. Neither these, nor any other documents or quotes cited herein, nor citations to any references, are admitted to be a prior art documents or citations.

REFERENCES

1. Ahlskog J E, Wright K F, Muenter M D, Adler C H (1996). Adjunctive cabergoline therapy of Parkinson's disease: comparison with placebo and assessment of dose response and duration of effect. *Clin. Neuropharmacol;* 19: 202–212.
2. Akpinar S (1987). Restless legs syndrome treatment with dopaminergic drugs. *Clinical Neuropharmacology;* 10:69–79.
3. Allen R P, Earley C J, Augmentation of the restless legs syndrome with carbidopa/levodopa. *Sleep* 1996; 19:205–213.
4. Becker P M, Jamieson A O, Brown W D, Dopaminergic agents in restless legs syndrome and periodic limb movements in sleep: response and complications of extended treatment in 49 cases, *Sleep* 1993;16:713–716.
5. Boghen D, Lamothe L, Elie R, Godbout R, Montplaisir J (1986). The treatment of restless legs syndrome with clonazepam: a prospective controlled study. *Can J Neurol Sci;* 13:245–247.
6. Boivin D B, Lorrain D, Montplaisir J, Effects of bromocriptine on periodic limb movements in human narcolepsy. *Neurology* 1993;43:2134–2136.
7. Bornstein B (1961). Restless legs. *Psychiat Neurol;* 141:165–201.1.
8. Brodeur C, Montplaisir J, Godbout R, Marinier R, Treatment of restless legs syndrome and periodic movements during sleep with L-dopa: a double-blind controlled study. *Neurology* 1988;38:1845–1848.
9. Brodeur C, Montplaisir J, Marinier R, Godbout R (1988). Treatment of RLS and PMS with L-dopa: a double-blind controlled study. *Neurology;* 35:1845–1848.
10. Callado-Seidel U, Krazenwadel J, Wetler T C, Kohnen R, et al., *Neurology* 1999;52:285–290.
11. Callaghan N (1966). Restless legs syndrome in uremic neuropathy. *Neurology* (Minn); 16:359–361.
12. Coleman R M (1982). Periodic movements in sleep (nocturnal myoclonus) and restless legs syndrome. In: Guilleminault C, (ed), *Sleeping and Waking Disorders: Indications and Techniques*.Menlo Park: Addison Wesley; 265–295.
13. Ekbom K A (1945). Restless legs. *Acta_Medica_Scandinauica;* suppl. 158: 1–123.
14. Ekbom K A (1960). Restless legs syndrome. *Neurology;* 10:868–873.
15. Fariello R G (1997). Pharmacodynamic and pharmacokinetic features of Cabergoline. *Drugs;* 55: S2, 10–16.
16. Frankel B, Patten B, Gillin C (1974). Restless legs syndrome. *JAMA;* 5 230:1302–1303.
17. Gorman C, Dyck P, Pearson J. (1965). Symptoms of restless legs. *Arch Intern Med;* 115:155–60.
18. Harriman D, Taverner D, Woolf A (1970). Ekbom's syndrome and burning paraesthesiae. *Brain;* 93:393–406.
19. Heiman E M, Christie M (1986). Lithium-aggravated nocturnal myoclonus and restless legs syndrome [letter]. *American Journal of Psychiatry;* 143:1191–1192.
20. Heinze F, Frame B, Fine C (1967). Restless legs and orthostatic hypotension in primary amyloidosis. *Arch Neurol;* 16:497–500.
21. Hening W, Chokverty S, Rolleri M, Walters A (1991). The cortical premovement potentials in RLS jerks. *Sleep Res;* 20:255.
22. Hening W A, Walters A, Kavey N, Gidro-Frank S, Cote L, Fahn S (1986). Dyskinesias while awake and periodic movements in sleep in restless legs syndrome: treatment with opioids. *Neurology;* 36:1363–1366.
23. Iannaccone S, Zucconi M, Marchettini P, Ferini-Strambi L, Nemni R, Quattrini A, Palazzi S, Lacerenza M, Formaglio F, Smirne S (1995). Evidence of peripheral axonal neuropathy in primary restless legs syndrome. *Mouement Disorders* 10:2–9.
24. Kaplan P W, Allen R P, Buchholz D W, Walters JK, A double-blind, placebo controlled study of the treatment of periodic limb movements in sleep using carbidopallevodopa and propoxyphene. *Sleep* 1993;16:717–723
25. Kotagal S, Chu J Y, O'Connor D M (1984). Nocturnal myoclonus—A sleep disturbance in children with leukemia. *Annals of Neurology;* 16:392.
26. Lugaresi E, Cirignotta F, Coccagna G, Montagna P (1986). Nocturnal myoclonus and restless legs syndrome. In: S Fahn et al. (eds), *Advances in Neurology*, vol.43: *Myoclonus*, New York: Raven Press; 295–307.
27. Martinelli P, Coccagna G, Lugaresi E (1987). Nocturnal myoclonus, restless legs syndrome, and abnormal electrophysiological findings. *Ann Neurol;* 21:515.
28. Matthews W B (1976). Iron deficiency and restless legs. *Br Med J;* 1:898.
29. Miyagi M, Itoh F, Taya F, Arai N, Isaji M, Kojima M, Uijie A (1996). Dopamine receptor affinities in vitro and stereotypic activities in vivo of cabergoline in rats. *Biol. Pharm. Bull.;* 19: 1210–1213.
30. Moldofsky H, Tullis C, Lue F A, Quance G, Davidson J (1984). Sleep-related myoclonus in rheumatic pain modulation disorder (fibrositis syndrome) and in excessive daytime somnolence. *Psychosomatic Medicine;* 46:145–151.
31. Montplaisir J, Godbout R, Boghen M D, DeChamplain J, Young S N, Lapierre G (1985). Familial restless legs with periodic movements in sleep: electrophysiological, biochemical, and pharmacological study. *Neurology;* 35:130–134.
32. Montplaisir J, Godbout R, Poirier G, Bedard M A (1986). Restless legs syndrome and periodic movements in sleep: physiopathology and treatment with L-dopa. *Clinical Neuropharmacology;* 9:456–463.
33. Mosko S S, Nudleman K L (1986). Somatosensory and brainstem auditory evoked responses in sleep-related periodic leg movements. *Sleep;* 9:399–404.
34. Ondo, William, "Ropinirole for Restless Legs Syndrome," *Movement Disorder;* 14: 138–140 (1999).
35. Reynolds G, Blake D R, Pall H S, Williams A (1986). Restless leg syndrome and rheumatoid arthritis. *British Medical Journal;* 292:659–660.
36. Ruiz-Primo E (1987). Is nocturnal myoclonus a common sleep disturbance in children with leukaemia. *Dev Med Child Neurol;* 29:833.

37. Salvi F, Montagna P, Plasmati R, Rubboli G, Cirignotta F, Veilleux M, Lugaresi E, Tassinari C A (1990). Restless legs syndrome and nocturnal myoclonus: initial clinical manifestation of familial amyloid polyneuropathy. *J Neurol Neurosurg Psychiatry;* 53:522–525.
38. Sandyk R, Bernick C, Lee S M, Stern L Z, Iacono R P, Bamford C R (1987). L-Dopa in uremic patients with the restless legs syndrome. *Int J Neurosci;* 35:233–235.
39. Spillane J D (1970). Restless legs syndrome in chronic pulmonary disease. *Br Med J;* 4:796–798.
40. Stiasny K., Oertel W. H., Schuiler P. (1998). Cabergoline in RLS, *ENS*, Nice, Abstract.
41. Thorpy M J. Chairman (1990). Diagnostic classification steering committee. In: "International classification of sleep disorders: diagnostic and coding manual." Rochester, Minn.: American Sleep Disorders Association.
42. Trenkwalder C, Stiasny K, Pollmacher T, Wetter T, Schwarz J, Kohnen R, Kazenwadel J, Kruger H P, Ramm S, Kunzel M, Oertel W H, L-dopa therapy of uremic and idiopathic restless legs syndrome: a double-blind, crossover trial. *Sleep* 1995; 18:681–688.
43. Trzepacz P T, Violette E J, Sateia M J (1984). Response to opioids in three patients with restless legs syndrome. *Am J Psychiatry;* 141:993–995.
44. von Scheele C (1986). Levodopa in restless legs. *Lancet;* 2:426–427.
45. von Scheele C, Kempi V, Long-term effect of dopaminergic drugs in restless legs. A 2-year follow-up. *Arch Neurol* 1990;47:1223–1224.
46. Walker S L, Fine A, Kryger M H, L-dopa/carbidopa for nocturnal movement disorders in uremia. *Sleep* 1996;19:214–218.
47. Walters A S, Hening W A, Chokroverty S, Gidro-Franck S. A double blind randomized crossover trial of bromocriptine and placebo in restless leg syndrome. *Ann Neurol;* 1988, 24:455–458.
48. Ware J C, Brown F W, Moorad P J, Pittard J T, Murphy M, Franklin D (1984). Nocturnal myoclonus and tricyclic antidepressants. *Sleep Research;* 13:72.
49. Watanabe S, Ono A, Naito H (1990). Periodic leg movements during either epidural or spinal anesthesia in an elderly man without sleep-related (nocturnal) myoclonus. *Sleep;* 13:262–266.
50. Wechsler L R, Stakes J W, Shahani B T, Busis N A (1986). Periodic leg movements of sleep (nocturnal myoclonus): an electrophysiological study. *Annals of Neurology;* 19:168–173.

SUMMARY OF THE INVENTION

Surprisingly and unexpectedly, it has been found that cabergoline and its pharmacologically acceptable salts thereof can be administered to patients in need thereof for the treatment of symptoms of restless leg syndrome (RLS). It is especially effective for the treatment of RLS patients who experience or who are susceptible to RLS augmentation and or tolerance. See the description and definitions of augmentation and tolerance, herein.

A favored treatment disclosed here for treatment of restless legs syndrome (RLS) in a patient suffering from or susceptible to such condition comprises the administration of an effective amount of the compound called cabergoline. The chemical name for the compound is 1((6-allylergolin-8β-yl) -carbony.)-1-(3-(dimethylamino)propyl)-3-ethylurea. Carbergoline is the active ingredient in DOSTINEX® or CABASER® Tablets, sold in the United States, Europe and Latin America as a treatment for hyperprolactinemic disorders and/or as a treatment for Parkinson's disease. The synthesis and use of cabergoline is disclosed and claimed in U.S. Pat. No. 4,526,892, which is incorporated herein by reference.

Conventional pharmaceutical preparations can be used, e.g., consisting essentially of an inert pharmaceutical carrier and an effective dose of the active substance; e.g., plain or coated tablets, capsules, lozenges, powders, solutions, suspensions, emulsions, syrups, suppositories, transdermal patch, etc. Preferred are tablets.

The effective dose range is 0.01 to 10.0 mg/day and patient, often more than 0.1 mg will be administered to a patient per administration and per day, and preferably between 0.25 to 10.0 mg/day, more preferably between 1 and 6 mg/day more preferably between 1 and 4 mg/day and even more preferably about 1 to 2 mg/day and patient p.o. While these levels above indicate mg/day, and typically they may be given once or twice a day, surprisingly, they may be given in these dosages on a less than daily basis. While the drug may be given once a day or twice a day, it might only be given three times a week, two times a week or even once a week for some patients. For less than daily dosing the tablet size or amount of administration of drug can vary and the mg of drug administered per patient may in fact be the mg/day dose suggested above. When given on a daily or less frequent schedule, the daily dosages mentioned here would be given only for the day of administration.

Patients with milder forms of RLS would be expected to need less drug, in some cases 0.05, 0.1 or more preferably 0.25 mg/day may be adequate. Patients with more severe forms of RLS and those who have been treated with other dopaminergic agents may be expected to need more drug.

The combination of cabergoline and levodopa is also disclosed.

Dosages should be increased gradually. Providing patients do not experience intolerable side effects, the dosage should be titrated to achieve a maximal therapeutic effect.

DESCRIPTION OF THE PREFERRED EMBODIMENTS

Cabergoline is a synthetic ergoline derivative, and a dopamine agonist. Cabergoline is a unique dopamine agonist with unusual properties. Most words used in this paper can be defined with definitions either commonly used or used by one skilled in the art. Here one skilled in the art would be a physician treating a patient with RLS or a RLS researcher, such as a PhD. scientist, considering or evaluating possible drug treatments for RLS. The authors will also provide some special definitions to better describe this invention.

Definitions

Dopamine receptors. Traditionally dopamine receptors were grouped into two "families" of receptors, D1 or D2, where the grouping was based upon pharmacological response. Using this type of nomenclature one would characterize cabergoline as a D2(D1) receptor agonist; meaning the drug acts on the D2 "family" of receptor sites but also had some affect on the D1 family. Oddly, cabergoline is unique in that it is a full D2 family agonist with partial DI family activity. More recently, with the advent of greater techniques in molecular biology, dopamine receptors have been catagorized into subfamilies based on their molecular binding attributes. Using this molecular receptor catagorization scheme the D1 physiology "family" may be said to have D1 and D5 molecular receptors and the D2 physiology "family" may be said to have D2, D3, D4 molecular receptors belonging to that family. Cabergoline can be said to bind to D2 and D3 molecular receptors with greater D2 over D3 binding. Scientists may discover or recognize even more families in the future. Scientists also know that different areas of the brain have different amounts of D1, D5, D2, D3, and D4 receptors but they do not fully understand how they are distributed among cell types, or the full physiological significance of their existence.

Dopaminergic agent is any chemical compound that acts like dopamine in the human body, and see dopaminergic agonist below. L-dopa or levodopa is a dopaminergic agent because it is converted into dopamine in the human body.

Dopamine agonist or Dopaminergic agonist is any drug or chemical compound that can stimulate a dopamine receptor, either through binding with the receptor or from binding or association with proteins or receptors that then bind or affect a dopamine receptor. A dopaminergic agonist may "act like dopamine in the human body" and hence be a dopaminergic agent but it need not be converted into dopamine, it may merely mimic some of the effects of dopamine because of its stimulation of dopamine receptors.

Cabergoline is described in U.S. Pat. No. 4,526,892, incorporated herein by reference. Unlike other D2 receptor family agonists, cabergoline is also pharmacologically unique in being a full D2 agonist with partial D1 activity. Cabergoline has a unique long duration of action of at least 24 hours or longer, Ahlskog J E, Wright K F, Muenter M D, Adler C H (1996). Adjunctive cabergoline therapy of Parkinson's disease: comparison with placebo and assessment of dose response and duration of effect. *Clin. Neuropharmacol;* 19: 202–212. (1996). Here we report that cabergoline may last as long as 65 hours and it may be an effective treatment for RLS for 65 hours or more, possibly as long as a week.

New Treatments For RLS

Here we report several new and surprising treatments useful for treating patients with RLS. Most importantly, cabergoline can be used for the treatment of RLS. Other new treaments for RLS include Lisuride a.k.a. DOPERGIN® as one compound and selegiline is another and the catagory of compounds known as COMT-inhibitors, including the drug entacapone represents yet another compound that can be used, either by themselves, or more preferably, in combination with L-dopa, or in one embodiment, in combination with cabergoline, or in another embodiment in combination with both L-dopa and cabergoline; for the treatment of RLS. All of these compounds and combinations should be administered in pharmaceutically effective amounts as determined by titration or methods ordinarly used by those skilled in the art. The use of cabergoline or its pharmaceutically acceptable salts in the manufacture of a medicament to treat RLS, and for any of the RLS symptoms described in herein is also disclosed as well as a pharmaceutical composition for use as a treatment of RLS, and for any of the RLS symptoms described herein.

Cabergoline is surprisingly effective for treating patents with RLS because of its long half life, and because it provides RLS sufferers benefits not provided by any other drug therapy.

I) The unique drug activity may provide for infrequent dosing. Unlike any other known compounds and especially other dopamine agonists, cabergoline can provide long lasting relief to patients suffering from RLS. Twice a day dosing can be effective but more preferred is once a day dosing, and in some cases dosing less than once a day may be possible. Some patients may get effective relief from dosing every other day or even just once a week. The cabergoline administration can be but does not have to be taken in the evening.

Surprisingly, cabergoline has been discovered to have a half life of 65 hours. This long half life will provide an unexpected benefit to RLS patients. Cabergoline may be effective when given daily, every other day, three times a week or even once a week. With some patients cabergoline may be given to an RLS patient only 1, 2 or 3 times a week, depending upon the specific patient and his or her individual response to the drug. Perhaps most surprisingly, in some patients, cabergoline will not need to be administered on a regular basis. Because of its unique properties discovered and described here, cabergoline could be admistered at different times of the day, and perhaps not even every day, rather than current treatments for RLS, which require a patent adhere to a strict schedule of dosing to maintain relief. For example, compare cabergoline with ropinirole, which some studies suggest should be given in doses of 1, 2 or 3 times a day to be effective. See, Ondo, William, "Ropinirole for Restless Legs Syndrome," *Movement Disorders;* 14: 138–140 (1999).

The effective dose range is 0.01 to 10.0 mg/day and patient, usually more than 0.1 mg will be administered to a patient per day, and preferably between 0.25 to 10.0 mg/day, more preferably between 1 and 6 mg/day more preferably between 1 and 4 mg/day and even more preferably about 1 to 2 mg/day and patient p.o. While these levels above indicate mg/day, and typically they may be given once or twice a day, surprisingly they may be given in these dosages on a less than daily basis. While the drug may be given once a day, twice a day, it might only be given three times a week, two times a week or even once a week for some patients. For less than daily dosing the tablet size or amount of administration of drug can vary and the mg of drug administered per patient may in fact be the mg/day dose suggested above. When given on a daily or less frequent schedule, the daily dosages mentioned here would be given only for the day of administration. It is expected that the treating physician will provide the patient with an appropriate amount of drug depending on various factors including the patient's weight, age, medical history, physiological condition, special needs, etc. and appropriate titration of the drug.

Patients with milder forms of RLS would be expected to need less drug, in some cases 0.05, 0.1, 0.5 or more preferably, 0.25 mg/day may be adequate. Patients with more severe forms of RLS and those who have been treated with other dopaminergic agents may be expected to need more drug.

In addition to a long half life, cabergoline appears to be effective as a monotherapy, without having to administer it with other drugs. In some cases patients being treated with multiple drug formulas, such as with levodopa administered twice a night or levodopa combined with a decarboxylase inhibitor such as carbidopa can instead be treated with only one medication, cabergoline. Although in some embodiments of this invention cabergoline plus levodopa is also disclosed as a novel treatment.

Cabergoline may be titrated for each patient but frequently it will need to be taken only once a day or less, and it may not even matter what time of day it is taken.

II) Here we report that cabergoline has a lower incidence of the deleterious side effects common with other RLS treatments, side effects known as augmentation or rebound. In addition to the descriptions above, augmentation or rebound is further described here.

Augmentation comprises: a) an earlier onset of RLS symptoms in the evening than before treatment, b) appearance of symptoms during the day, c) an involvement of other body parts, typically the arms, or d) an increased severity and may develop even shortly after onset of levodopa therapy. The incidence of augmentation appears greater in patients with severe RLS and under higher levodopa dosages.

In one form, augmentation in RLS patients can be described as an increase in the severity of daytime RLS symptoms following a decrease in the night time symptoms after typical evening administration of drug treatment. More broadly augmentation can refer to any increase in RLS symptoms that follow an initial decrease in symptoms following drug. It can appear in a patient responding well in the first few days or weeks of treatment but who then has an an increase rather than a decrease in severity of symptoms. Augmentation and/or rebound have often been observed when RLS patient is treated with a drug that is a dopaminergic agent such as levodopa or some dopamine agonists such as pergolide, bromocriptine, etc. Augmentation has been reported to occur in L-dopa treated patients at rates of 27% in a 12 week study, see, Callado-Seidel U, Krazenwadel J, Wetler T C, Kohnen R, et al., *Neurology* 1999; 52:285–290, and 82% of RLS patients in a different study, see, Allen R P, Earley C J, *Sleep* 1996; 3:205–213. In this latter study, augmentation occurred in 31% of PLMS patients (periodic limb movements of sleep) and 82% of RLS patients. 50% of RLS patients with augmentation required a medication change. Of the 22 RLS patients with augmentation, 100% of these patients reported 3 major symptoms of increased severity. The increased symptoms included: a) temporal expansion—symptoms that occurred at bedtime now occur earlier in the evening. In some, it extended a full 24 hours, b) increase in intensity—mild symptoms at bedtime or evening became distressing, c) decrease in the time at rest when symptoms occur and 7% of patients reported increased movement in other body parts.

Rebound phenomena is similar to augmentation with the appearance of RLS symptoms in the morning hours early after awakening. Some physicians attempt treatment by switching to a sustained release preparation of drug and/or by adding a morning dose of levodopa. It has to be pointed out that the problem of rebound is different from a single loss of efficacy during the night, which is also observed in some especially severely affected patients.

There are reports that the dopamine agonist pergolide had some effect in patients who developed augmentation under levodopa in a 6 month open label trial. On the other hand, augmentation was also reported in patients treated with pergolide (again responsive to dopaminergic agents) but to a lower degree and less severe in two open trials with a follow-up period of 6 to 28 and 2 to 39 months respectively. In one study 15% of patients treated with pergolide suffered from augmentation, see, Earley C J, Allen R P. Pergolide and carbidopallevodop were used in the treatment of the restless legs syndrome and periodic leg movements in sleep in a consecutive series of patients. In this study, 21 of 51 patients responded to levodopa, 26 of 51 switched to pergolide, 19 of 26 pergolide patients responded well however, 4 of 26 pergolide patients had augmentation. It appeared PLMS patients responded well to 1-dopa, RLS responded to pergolide.

It is unclear why some patients do develop rebound phenomenon or augmentation and some do not. Clearly what is needed is a medication where the patients and the treating physician have some assurance that augmentation will not occur. While the authors here make no guarantees that augmentation will never occur with cabergoline treatment, it is much less likely that augmentation or rebound will occur to patients being treated with cabergoline than with patients being treated with other dopaminergic agents such as levodopa or pergolide. Cabergoline appears to have fewer of the augmentation or rebound side effects known to trouble patients taking other drug treatments. The augmentation or rebound side effect can be a most unpleasant one, with a patient knowing that the price he or she must pay for having his or her symptoms relieved initially, may be a greater intensity of symptoms later. A patient experiencing augmentation or rebound may get relief at night, possibly allowing sleep, only to experience two or three times the usual number of periodic leg movements the next day. A patient experiencing augmentation or rebound effects would instead probably prefer to be treated with cabergoline than with a treatment where they have to "rob Peter to pay Paul" for a decent nights sleep.

III) We also report here that cabergoline may be very useful in treating the symptoms of RLS long after treatments with other dopaminergic agents and dopamine agonists, such as L-dopa have become ineffective due to a patient's tolerance to the drug treatment.

Tolerance in RLS patients can be described as accomodation to a drug therapy. This means either more and more drug is needed to relieve the same symptoms that were previously treated with smaller amounts of drug or where the same amount of a drug provides less and less relief from the symptoms being treated. Tolerance is known to occur with levodopa treatment of patients suffering from RLS. Tolerance to a drug usually is apparent after from about 3 to 6 months treatment with a drug. Tolerance to levodopa is common.

Unlike previously known dopamine agonists, treatment with cabergoline provides long lasting relief from the symptoms of RLS with low tolerance. This means effective treatment can be maintained without large increases in the amount of drug that needs to be provided to the patient. In most cases once titration with cabergoline demonstrates a clinical effect, medication will not need to be increased.

IV) Cabergoline provides improved sleep patterns in patients with abnormal sleep patterns. Cabergoline is especially useful in normalizing the sleep patterns of patients with RLS. Many patients with RLS have abnormal sleep patterns and the more severe the symptoms of the RLS, the worse these patients sleep. In perhaps its greatest benefit to ailing patients with RLS, cabergoline can provide these patients with a good night sleep.

Cabergoline is thus seen to provide long lasting and improved treatment, with convenient and infrequent dosing without the unpleasant side effects frequently seen with other RLS treatments. Cabergoline can frequently be given as a monotherapy as opposed to having to combine it with another dopaminergic agent as is frequently done. Note that for some patients; however, we also disclose here the use of, or the preparation of, a medicament or treatment comprising the combination of cabergoline and dopaminergic agent including levodopa, and or the other dopaminergic agonists mentioned in the document, including the background section, combinations of drugs used in pharmacologically acceptable amounts, and more preferably, in the amounts for cabergoline alone disclosed above for cabergoline and for levodopa as would normally be administered by one skilled in the art when administering levodopa or one dopaminergic agent with another dopaminergic agent.

Expected Results

In a 12-week open label pilot trial, the effects of a single evening cabergoline-dose on symptoms of RLS were investigated in 9 patients and the results presented here. See also, Stiasny K., Oertel W. H., Schuiler P. (1998). Cabergoline in RLS, *ENS*, Nice, Abstract. To evaluate the efficacy and tolerability of this long-acting dopamine (D1)/D2 agonist, cabergoline, (half-life >65 hours), we investigated 9 patients who previously had insufficiently been treated with and partly developed augmentation under levodopa in an open label pilot trial.

Efficacy was assessed by polysomnography and subjective ratings. All patients previously had experienced partial benefit of a levodopa therapy (either standard or standard and slow release) and in part developed augmentation under levodopa therapy. At study entry all patients were comedicated with domperidone (20 mg TID) and five were still under levodopa therapy (400–800 mg). At the endpoint all patients were on cabergoline monotherapy (mean dose 2.1 mg, range 1 to 4 mg). Domperidone was stopped in all patients due to excellent tolerability. Polysomnographic data showed a significant reduction of the number of periodic leg movements (PLM) during time in bed, PLM arousals and PLM awakenings. Total sleep time was prolonged, sleep latency shortened and sleep efficiency increased. All patients reported significant relief or became free of RLS symptoms. These results indicate that cabergoline given as a single evening dose is effective and well tolerated in restless legs syndrome especially in patients with severe RLS and those who developed augmentation under levodopa therapy. In addition to the relief from the symptoms of RLS reported above there is another significant benefit from the administration of cabergoline for the treatment of RLS. Many patients who receive L-Dopa or L-Dopa plus dopa-decarboxylase-inhibitor have benefitted from short term relief from the symptoms of RLS, albiet frequently with the rebound and or augmentation affects mentioned above, but then they become "tolerant" to the treatment and after a period of time usually 6 months or less they no longer respond well to the treatment. This could be represented in visual form by a graph that plotted relief from RLS symptomatic events against time, a with a treatment at time zero. As time runs to 6 months or more after treatment with L-Dopa, the data would provide a graph showing a line that gradually slopes from a high point beginning with the treatment to a low point after 6 months or more of treatment. Conversely, as time runs to 6 months or more after treatment with cabergoline, the data would provide a graph showing a line that has much less of a slope, with cabergoline than with L-Dopa, from a high point beginning with the treatment to a low point after 6 months or more of treatment. This lack of tolerance with treatment from cabergoline is most surprising and unexpected.

Cabergoline for the treatment of RLS can be given in the dose range of from 0.1 and more preferably 0.25 to 6 mg per person per day, with 1–4 mg/person per day preferred and 1–2 mg more preferred. Cabergoline may, with some patients, also be given every other day, at these dosages and still provide relief from RLS. Described here is a method for the preparation of a medicament useful for the treatment of RLS. The medicament can be prepared using cabergoline as the active ingredient plus standard excipients, formulations and preparations known to one skilled in the art.

Cabergoline can be provided to patients never before treated from RLS or it can be given to patients previously treated with any other medications, especially those mentioned in the Background section of this document. Cabergoline is especially useful to patients suffering from symptoms of the disease who have previously been treated with a D2 agonist or levodopa or L-dopa or who are currently being treated with such compounds.

RLS patients experiencing 2–8 Periodic Leg Movements (PLM) per hour during sleep are especially good candidates for cabergoline therapy and patients experiencing 3–7, 4 or 5 PLM/hr are also preferred candidates for the drug. The above description should fully describe this invention and enable one skilled in the art to practice it. Obvious variants and combinations of the invention with treatments mentioned in the Background section are expected and described here. In addition, an example is provided to further illustrate the invention. The descriptions provide guidance as to similar studies that could be performed and expected results. Obvious variations of this example should be apparent to one skilled in the art.

EXAMPLE

Following a 2-week baseline period, all patients were treated with cabergoline in an open trial for 12 weeks. Apart from levodopa, patients had to stop taking any medication known to have positive or negative effect on RLS two weeks before baseline (i.e., other dopamine agonists, benzodiazepines, opioids or other psychotropic agents). Patients who were on levodopa therapy were allowed to either stop levodopa prior to study entry or to continue, taper or discontinue levodopa during the study. To prevent well known peripheral dopaminergic side-effects such as nausea, vomiting, vertigo and arterial hypotension domperidone (not available in the United States) was comedicated initially and also tapered if possible. Cabergoline was started with 0.5 mg as a single evening dose given two hours prior to bedtime and was increased in steps of 0.5 mg until RLS symptoms clearly improved or disappeared, in the patients' opinion. In levodopa treated patients, levodopa was gradually decreased and discontinued if possible. Neurological case history, examination, electrocardiogramm, chest x-ray and polysomnography were performed to ensure that selection criteria were fulfilled. A two-night PSG (including one night of adaptation) was performed to evaluate the diagnosis and inclusion/exclusion criteria regardless if patients were on or off levodopa. After a 12-week treatment period patients were studied again for one night in the sleep laboratory. Subjective ratings were obtained at baseline, week 4, week 8 and at the endpoint after 12 weeks. In addition patients were monitored by phone calls to note any adverse events and to determine whether to increase the dosage of the study drug, to decrease levodopa and to decrease domperidone. The time schedule of phone calls was variable and the frequency mostly dependent on the presence of simultaneous levodopa therapy.

Inclusion criteria. Patients were included if they fulfilled the minimal diagnostic criteria according to the International RLS Study Group. After rating clinical symptoms at baseline, patients were referred to polysomnography without any RLS specific treatment other than levodopa. Patients were included if they had more than five PLM per hour of time-in-bed (PLM index) and a sleep efficiency index (total sleep time per hour time-in-bed) of less than 85%.

Exclusion criteria. Patients with signs of any other sleep disorder on PSG, especially sleep apnea syndrome (respiratory disturbances index >5 per hour total sleep time), were excluded. Subjects receiving neuroleptic, antidepressant or other psychotropic medications or with any severe additional illness (with special consideration to pulmonary fibrosis) or drug abuse were also excluded. Patients with established or suspected hypersensitivity to ergot derivates and patients with clinical significant change in routine laboratory studies were not included. Pregnant or lactating women or women without safe contraception were not allowed to participate in this study.

Dosing. Study medication was available in tablets containing 0.5 mg, 1 mg or 2 mg Cabergoline (Cabaseril®, Pharmacia & Upjohn, Erlangen, Germany). Medication was taken 2 hours prior to bedtime. Initial therapy consisted of one 0.5 mg tablet. Patients could increase the dosage in steps of 0.5 mg if they considered that their RLS symptoms including sleep impairment had not sufficiently improved within 3 days. The increased dose could be decreased again if necessary. All patients were initially comedicated with domperidone 20 mg t.i.d. which could be tapered and stopped if possible. Subjects who were pretreated with levodopa were asked to decrease levodopa simultaneously if possible.

Polysomnographic studies. At baseline and at the study end after 12 weeks PSG recordings were performed for one night (11 p.m.–7 a.m.) to evaluate inclusion/exclusion criteria and to obtain primary and secondary efficacy parameters. Studies included monitoring of electroencephalogram (EEG) (C3-A2, C4-A1), electrooculogram, chin EMG, EMG of both anterior tibialis muscles and electrocardiogram (ECG). PSG methods used standard procedures such as Pollmacher and Schultz. At baseline respiration, oronasal airflow, respiration effort and oxygen saturation were monitored by standard methods. Sleep scoring was also done by methods. PLM were scored if being part of a series of at least four consecutive movements lasting 0.5–5 seconds, with an interevent interval of 4 to 90 seconds. PLM index was calculated as number of PLM per hour time in bed and PLM arousal index as number of PLM arousals per hour total sleep time. Sleep efficiency was computed as total sleep time per hour of time in bed and sleep onset as timepoint of the first period of NREM 2 lasting at least 3 minutes.

Subjective ratings. After each night of recording and at each visit at week 2 and 4, patients rated the severity of illness (normal to extremely ill), the therapeutic effects by rating their global improvements by use of the Patients Global Impressions (general condition very much worse to very much better), the severity of RLS symptoms during the time of falling asleep, during the night and during the day (scale: 0=not present to 10=very strong) and sleep satisfaction (very unsatisfied to very satisfied). In addition patients rated their quality of life, concerning well being and complaints during the previous week, using modified 50-mm Hamburger Visual Analogue Scale. Patients also filled in a sleep diary at each study visit rating the following symptoms: global assessment of sleep (very bad to very good night), sleep latency, sleep time, frequency of awakenings and urge to move the legs at time falling asleep, during the night and during the day (scale: 0=not present to 10=very strong).

Physician's rating. The physician rated the severity of illness at baseline (normal to extremely ill), the global improvement (general condition very much worse to very much better) and the side effects by use of the Clinical Global Impressions (CGI). Safety. Safety of Cabergoline was assessed to the type and frequency of adverse event, clinically significant changes in laboratory data or ECG and premature discontinuation of study participation. Adverse events were classified as serious versus nonserious and characterized by intensity, relationship to drug treatment, frequency, course and therapeutic intervention.

Statistical analysis. Statistical evaluation was performed as intent-to-treat analysis using descriptive statistics.

The actual results of this example are as follows:

Subjects. Nine patients (seven women and two men, mean age 54.1±8.7, range 38.1–64.3 years) with idiopathic RLS for 23.1±13.7 years (range 5–47 years) participated. They previously had been treated insufficiently with levodopa despite several attempts of adjustment. At study entry five patients were on levodopa with dosages ranging from 400–800 mg. All of them had developed augmentation under levodopa. The remaining four patients were off any specific RLS medication during baseline investigation. Two patients had been previously treated with other dopamine agonists, one developping severe arterial hypotension under low dosage of bromocriptine (5 mg). At baseline conditions the physician considered the patients to be extremely ill (2), very ill (4) or markedly ill (3).

Medication and dosage. At the end of the study (range 84–89 days) all patients were on Cabergoline monotherapy (mean dosage 2.1 mg) with dosages ranging from 1.0 to 3.0 mg in 8 patients (1 mg in 2; 1.5 mg in 1; 2 mg in 3; 2.5 mg in 1; 3 mg in 1). One patient who entered the study with 800 mg levodopa finally required 4.0 mg Cabergoline. Cabergoline was given q.d. in the evening between 7 and 9 p.m. All patients who initially were on levodopa discontinued levodopa treatment during the study. Domperidone was stopped in all patients due to good tolerability.

Efficacy. Polysomnography: Analysis of the two primary endpoints showed a superior effect of Cabergoline compared to baseline measurements for the following parameters: 1) the total number of PLM during time in bed was significantly reduced from 195.8±109.1 to 26.4±40.2 and 2) total sleep time was prolonged by more than one hour from 302.7±50.7 minutes to 379.4±59.8 minutes. Secondary polysomnographic efficacy parameters revealed a pronounced increase in sleep efficiency (63.1±10.5% to 79.1±12.5%) and sleep latency was shortened by almost half an hour (42.4±49.1 vs. 16.3±22.8 minutes). Other PLM parameters revealed a significant reduction of the PLM index (27.7±17.1 vs. 3.6±5.3), the PLM arousals (51.7±42.3 vs. 6.4±11.2), the PLM arousal index (10.4±7.8 vs. 1.0±1.7) and the number of PLM awakenings (9.6±4.9 vs. 1.0±2.0) (See Table 1).

Subjective ratings of sleep and RLS: Under Cabergoline monotherapy the severity of illness was rated to be much less pronounced since patients rated themselves as normal (5) or borderline (2) in PGI, only two as moderately ill compared to baseline when patients rated themselves as extremely (2), very (4) or markedly (3) ill. General condition was rated to be very much better (6) or much better (3) in PGI under Cabergoline. Global ratings of RLS severity for the last week of each study visit showed that RLS symptoms significantly improved during the time of falling asleep (4.9±4.3 vs. 0.4±0.7), during the night (6.7±2.7 vs. 1.6±2.6) and during the day (5.1±3.4 vs. 0.8±1.7). All patients reported a significant relief or became free of RLS symptoms. At the endpoint patients were much more satisfied with their sleep since 2 were very, 4 markedly, 1 moderately satisfied and only 2 moderately unsatisfied compared to baseline conditions when all patients were very (1), markedly (6) or moderately (2) unsatisfied with their sleep.

In the sleep diaries the global quality of the previous night was rated much higher at endpoint (6.9) than at baseline (3.1) on a zero (very bad) to 10 (very good) scale. Patients also had to get up less often (0.6 times) under cabergoline monotherapy (vs. 2.1 times per night at baseline).

Subjective ratings of quality of life: Hamburger Visual Analogue Scales can be subdivided into six scales measuring life satisfaction and six measuring negative feelings and complaints. Patients rated their quality of life much better than under baseline conditions on a four I five item list.

Physician's rating of severity of RLS. Physician's rating showed a significant global improvement. General condition of the patients was rated to be very much better in 5, much better in 3 and minimally better in 1 patients under Cabergoline.

Safety. Adverse events: A total of 8 adverse events probably related to the study drug were reported in 5 patients. Probably related side effects were vertigo (2), dizziness (2), headache (2), diarrhea (1) and nausea in 1 patient, latter leading to temporary dose reduction of cabergoline. There were no serious side effects and no patient withdrew from the study. All adverse events were temporary and considered to be mild to moderate. No significant changes were detected in laboratory data or in ECG. Since overall tolerability was excellent all patients could taper and finally stop domperidone.

Discussion. The results of this open label pilot trial show for the first time that the long-acting dopamine (D1)/D2 agonist cabergoline is very effective and well tolerated in the treatment of restless legs syndrome. A 12-week treatment period with a single evening dose of 1 to 4 mg (mean 2.1 mg) cabergoline resulted in a complete or significant relief of RLS symptoms and a marked improvement of subjective and objective sleep parameters in all patients who previously had been insufficiently treated with levodopa. In two patients who had complete relief of RLS symptoms subjective sleep quality improved but they were still moderately unsatisfied with their sleep. Reduction of the cabergoline dosage could further improve sleep in these patients without worsening of RLS symptoms suggesting the well known alerting effect of dopamine agonists as underlying cause. Augmentation of RLS symptoms evoked by levodopa was reversible under cabergoline in all of our patients. Due to good tolerability domperidone was tapered and finally stopped in all patients. There were no serious adverse events and no patient discontinued the study because of side effects. In addition we did not see peripheral or other dopaminergic side effects under 4 mg cabergoline monotherapy.

Several recent studies including double-blind placebo controlled trials have indicated that levodopa provides an effective treatment of restless legs syndrome and therefore it is gaining increasing acceptance as the treatment of choice in RLS. Due to the short half-life (2 to 4 hours) regular release formulas often do not maintain therapeutic coverage throughout the night. Attempts to deal with this difficulty have been made, by the attempt to create a sustained release formula for levodopa. Major problems may further complicate levodopa therapy especially in patients with severe RLS. In this relatively short treatment period we did not observe augmentation in our patients. Although the sample size is limited our results show that 1) cabergoline is effective in the treatment of RLS, 2) that it is also effective in patients with severe RLS and most important 3) that it is effective in patients who develop augmentation under levodopa therapy.

Cabergoline is the first chemical agent to provide 24-hour efficacy in the therapy of RLS.

TABLE 1

Results of polysomnographic data at baseline(five out of nine patients being on levodopa therapy) compared to the endpoint on cabergoline monotherapy

|  | Baseline | Week 12 |
| --- | --- | --- |
| Sleep Latency (min) | 42.4 ± 49.1 | 16.3 ± 22.8 |
| Total sleep time (min) | 302.7 ± 50.7 | 379.4 ± 59.8 |
| Sleep efficiency (%) | 63.1 ± 10.5 | 79.1 ± 12.5 |
| No. Of PLM | 195.8 ± 109.1 | 26.4 ± 40.2 |
| PLM index | 27.7 ± 17.1 | 3.6 ± 5.3 |
| PLM arousal | 51.7 ± 42.3 | 6.4 ± 11.2 |
| PLM arousal index | 10.4 ± 7.8 | 1.0 ± 1.7 |
| PLM awakening | 9.6 ± 4.9 | 1.0 ± 2.0 |

What is claimed is:

1. A method for treating restless legs syndrome (RLS) in a patient suffering from RLS, and in need of an effective treatment thereof, comprising: the administration of an effective amount of cabergoline or a pharmacologically acceptable salt thereof.

2. A method of claim 1, wherein the dose of cabergoline is about 0.1 to 6 mg per patient per administration, on an as needed basis.

3. A method of claim 2 wherein the dose of cabergoline is administered once a day.

4. A method of claim 2 wherein the dose of cabergoline is administered 4 or 5 times a week in amounts from about 0.25 to 6 mg per administration.

5. A method of claim 2 wherein the dose of cabergoline is administered 2 or 3 times a week in amounts from about 0.25 to 6 mg per administration.

6. A method of claim 5 wherein the dose of cabergoline is administered once a week in amounts from about 0.25 to 6 mg per administration.

7. A method of claim 1, wherein the dose of Cabergoline is about 0.25 to 4 mg/day.

8. A method of claim 1, wherein the dose of Cabergoline is about 0.25 to 2 mg/day.

9. A method for treating restless legs syndrome (RLS) in a patient suffering from RLS, who has previously been treated, or is concurrently being treated with one or more of; a dopamine agonist, a benzodiazepine, or a psychotropoic agent, comprising: the administration of an effective amount of cabergoline or a pharmacologically acceptable salt thereof.

10. A method of claim 9, wherein the previous or concurrent treatment is or was with a dopamine agonist and the dose of Cabergoline is about 0.1 to 6 mg/day.

11. A method of claim 9, wherein said dopamine agonist is or was levodopa.

12. A method of claim 11, wherein the dose of Cabergoline is about 0.25 to 4 mg/day.

13. A method of claim 9, wherein said previous or concurrent treatment is or was with a benzodiazepine and the dose of Cabergoline is about 0.25 to 4 mg/day.

14. A method of claim 13, wherein said benzodiazepine is clonazepam (Klonopin).

15. A method of claim 9, wherein said previous or concurrent treatment is or was with said psychotropoic agent, wherein said psychotropoic agent is an opioid and the dose of Cabergoline is about 0.1 to 4 mg/day.

16. A method for treating restless legs syndrome (RLS) in a patient suffering from RLS, where the patient has suffered from or is considered susceptible to suffer from agumentation or rebound effects from a previous treatment for RLS wherein the previous treatment consists of being treated with one or more of; a dopaminergic agent, a dopamine agonist, a benzodiazepine, or a psychotropoic agent, comprising: the administration of an effective amount of cabergoline or a pharmacologically acceptable salt thereof.

17. A method of claim 16 where said effective amount of cabergoline is between about 0.25 to 5 mg per patient per day.

18. A method of claim 16 where said previous treatment consisted of being treated with a dopamine agonist, wherein said dopamine agonist is levodopa and said effective amount of cabergoline or salt thereof is from 0.25–4 mg per patient per day.

19. A method for treating restless legs syndrome (RLS) in a patient suffering from RLS, where the patient has suffered from tolerance from a previous treatment for RLS wherein the previous treatment consisted of being treated with one or more of; a dopaminergic agent, a dopamine agonist, a benzodiazepine, or a psychotropoic agent, comprising: the administration of an effective amount of cabergoline or a pharmacologically acceptable salt thereof.

20. A method of claim 19 where said previous treatment consisted of being treated with a dopamine agonist, wherein said dopamine agonist is levodopa and said effective amount of cabergoline or salt thereof is from 0.1–4 mg per patient per day.

21. A method for treating restless legs syndrome (RLS) in a patient suffering from RLS, and in need of an effective treatment thereof, comprising: the administration of an effective amount of cabergoline or a pharmacologically acceptable salt thereof in combination with an effective amount of levodopa or its pharmacologically acceptable salts.

22. A once a day method for treating restless legs syndrome (RLS) in a patient suffering from RLS, and in need of an effective treatment thereof, comprising: the administration of an effective amount of cabergoline or a pharmacologically acceptable salt thereof to the patient, once a day.

23. A method for treating restless legs syndrome (RLS) in a patient suffering from RLS, and in need of an effective treatment thereof, comprising: the administration of an effective amount of cabergoline or a pharmacologically acceptable salt thereof, but without the administration of another dopaminergic agent.

24. A method for treating restless legs syndrome (RLS) in a patient suffering from RLS, and in need of an effective treatment thereof, consisting essentially of: the administration of an effective amount of cabergoline or a pharmacologically acceptable salt thereof.

* * * * *